United States Patent
Gadini et al.

(10) Patent No.: US 7,124,039 B2
(45) Date of Patent: Oct. 17, 2006

(54) DEVICE COMPRISING DETECTING MEANS FOR HYDRAULIC OR CHEMICAL-PHYSICAL PROPERTIES OF A FLUID

(75) Inventors: Costanzo Gadini, Frassineto Po (IT); Andrea Fiorini, Casale Monferrato (IT)

(73) Assignee: Eltek S.p.A., Casale Monferrato (Alessandria) (IL)

( * ) Notice: Subject to any disclaimer, the term of this patent is extended or adjusted under 35 U.S.C. 154(b) by 0 days.

(21) Appl. No.: 11/014,796

(22) Filed: Dec. 16, 2004

(65) Prior Publication Data

US 2005/0107013 A1    May 19, 2005

Related U.S. Application Data

(63) Continuation of application No. PCT/IB03/02690, filed on Jun. 13, 2003.

(51) Int. Cl.
*G01F 23/00*     (2006.01)
*G01N 11/00*     (2006.01)

(52) U.S. Cl. ............................ 702/50; 702/45; 702/100; 702/114; 73/863.02

(58) Field of Classification Search ................ 702/45, 702/50, 54, 56, 75, 100, 104, 114, 116; 73/861, 73/861.04, 861.77, 863.01, 863.02, 861.33; 137/3, 39, 101.21, 115.25, 119.06
See application file for complete search history.

(56) References Cited

U.S. PATENT DOCUMENTS

| 5,086,806 A | 2/1992 | Engler et al. |
| 6,387,424 B1 * | 5/2002 | Funk .......................... 426/231 |
| 2005/0109792 A1 * | 5/2005 | Fiorini et al. .................. 222/1 |

FOREIGN PATENT DOCUMENTS

| GB | 2 308 947 A | 7/1997 |
| WO | WO 01 89318 A | 11/2001 |

* cited by examiner

*Primary Examiner*—Bryan Bui
(74) *Attorney, Agent, or Firm*—Sughrue Mion, PLLC

(57) ABSTRACT

A device has a body defining a space for the passage of a fluid, as well as a detector of a hydraulic or chemical-physical property of the fluid in the space. The detector is connected to a control unit by means of a wireless communication system that includes a data transmission circuit, connected to the detector, and a data receiving circuit, interfaced to the control unit. The wireless communication system includes a radio-frequency passive electric circuit without independent power supply.

42 Claims, 11 Drawing Sheets

DEVICE COMPRISING DETECTING MEANS FOR HYDRAULIC OR CHEMICAL-PHYSICAL PROPERTIES OF A FLUID

The present application is a Continuation of International Application PCT/IB03/02690, with an international filing date of Jun. 13, 2003, the disclosure of which is incorporated into this application by reference; the present application is further based on Italian Patent Application No. TO2002-A000517 filed on Jun. 17, 2002, the disclosure of which is also incorporated into this application by reference.

BACKGROUND OF THE INVENTION

1. Field of the Invention

The present invention refers to a device comprising a body defining a space containing or allowing the passage of a fluid, said body being associated to detecting means of at least a hydraulic or chemical-physical property of the fluid present in said space, the detecting means being operatively associated to a control system of the device.

2. Description of the Related Art

Some hydraulic devices, such as for instance some types of electric valves, integrate a flow meter designed to measure the flow rate of a fluid under control or to be treated by said device. Conversely, other hydraulic devices integrate detectors of one or more chemical-physical properties of a fluid, for instance some decalcifying devices for household appliances, which are associated to detecting means for water hardness. An application field exemplifying the problems underlying the present invention comprises mixing valves, and in particular those used for drink vending machines.

Some drinks, such as for instance non-alcoholic drinks, consist of a mixture of at least two liquid ingredients, usually a concentrated syrup and water, the latter suitably diluting the syrup. In some drink vending machines, the so-called post-mix type, syrup and water are mixed directly by the consumer, or by an operator, on the spot where the vending machine is installed. A post-mix vendor therefore comprises a device mixing the two components straight before they are supplied to the consumer. Said mixing device typically comprises at least two electric valves, for water and syrup respectively, installed so as to operate together and generally integrated into one module shaped as a mixing valve.

Some mixing valves used in the aforesaid field envisage the detection of hydraulic or chemical-physical properties of the water-syrup mixture. In particular, some applications envisage the use of flow meters for syrup and water, so as to measure the instantaneous flow rate of the fluid ingredients and to adjust the mixing ratio consequently by acting onto the mixing valve. In other applications the mixing operation is based on the measurement of the percentage of sugar, usually known as "Brix", present in a final mixture comprising known ratios of water and syrup. In further systems, conversely, the mixing operation is regulated on the basis of the measurement of electric conductivity (see for instance U.S. Pat. No. 6,387,424) or refractive index (see for instance U.S. Pat. No. 6,374,845) referred to the mixture of water and syrup.

The integration into the mixing valve of means required to detect said quantities involves the presence of electric connections and contacts between said sensors and the control system supervising the operation of the valve. The presence of cables, beyond making the installation of the device quite complex and having given overall dimensions, limits the positioning of the detecting means within the valve. The electric contacts between the detecting means and the corresponding supply and/or signal cables then undergoes wear and tear in time, typically due to oxidation, considering that said devices often operate in moist environments; that is why high requirements of electric insulation are to be met. The presence of connections and contacts eventually involves the risk of unintentional dispersions of electric currents that can be dangerous, above all if we consider that said detecting means have to be put in contact with the liquid to be measured (for instance sensors of conductivity, refractive index, and so on). The presence of electric contacts further makes the separation and/or removal of components of the device quite difficult, for instance to washing and/or maintenance purposes.

The same applies also to the integration into a mixing valve as described before of a flow or flow rate sensor, aiming at enabling the measurement of the amount of one or more of the liquid ingredients used.

SUMMARY OF THE INVENTION

In general terms, the present invention envisages to carry out a hydraulic device enabling to obviate the aforesaid drawbacks of the prior art. An additional aim of the invention is to suggest a hydraulic device in which the control of hydraulic or chemical-physical properties of one or more fluids can take place in a convenient, simple, safe and accurate way.

A further aim of the invention is to carry out a hydraulic device in which the control of hydraulic or chemical-physical properties of one or more fluids can take place without preventing the possibility of an easy assembly/reassembly of components of the device integrating detecting means, in particular without disconnecting/reconnecting the electric contacts to the detecting means.

These and other aims, which shall be evident in the following, are achieved according to the present invention by means of a hydraulic device having the characteristics of the appended claims, which are regarded as an integral part of the present description.

BRIEF DESCRIPTION OF THE DRAWINGS

Further aims, characteristics and advantages of the present invention shall be evident from the following detailed description and from the accompanying drawings, provided as a mere explaining non-limiting example, in which.

DESCRIPTION OF PREFERRED EMBODIMENTS OF THE INVENTION

In the following description we shall first refer to a control and/or mixing device for fluid, for instance drink, vending machines, which envisages the detection and control of the quality of said fluids, i.e. drinks, however taking for granted that the applications of the invention comprise a large group of hydraulic devices for the treatment and/or control of fluids and mixtures, not necessarily of food origin.

With reference to FIGS. 1 to 4, the numeral 1 globally refers to a hydraulic device carried out according to the invention; in the case disclosed in the example, the device 1 is a double electric mixing valve for post-mix vendors, designed to be used in a drink vendor; in said example the device 1, therefore, is used for preparing a drink consisting of two liquid ingredients, in particular water and syrup, and acts by (I) receiving and controlling the flow of the first liquid ingredient through a first electric valve, (II) receiving and controlling the flow of a second liquid ingredient through a second electric valve, and (III) mixing said two ingredients so as to form the mixture, and supplying the latter to a consumer.

Figure 1:
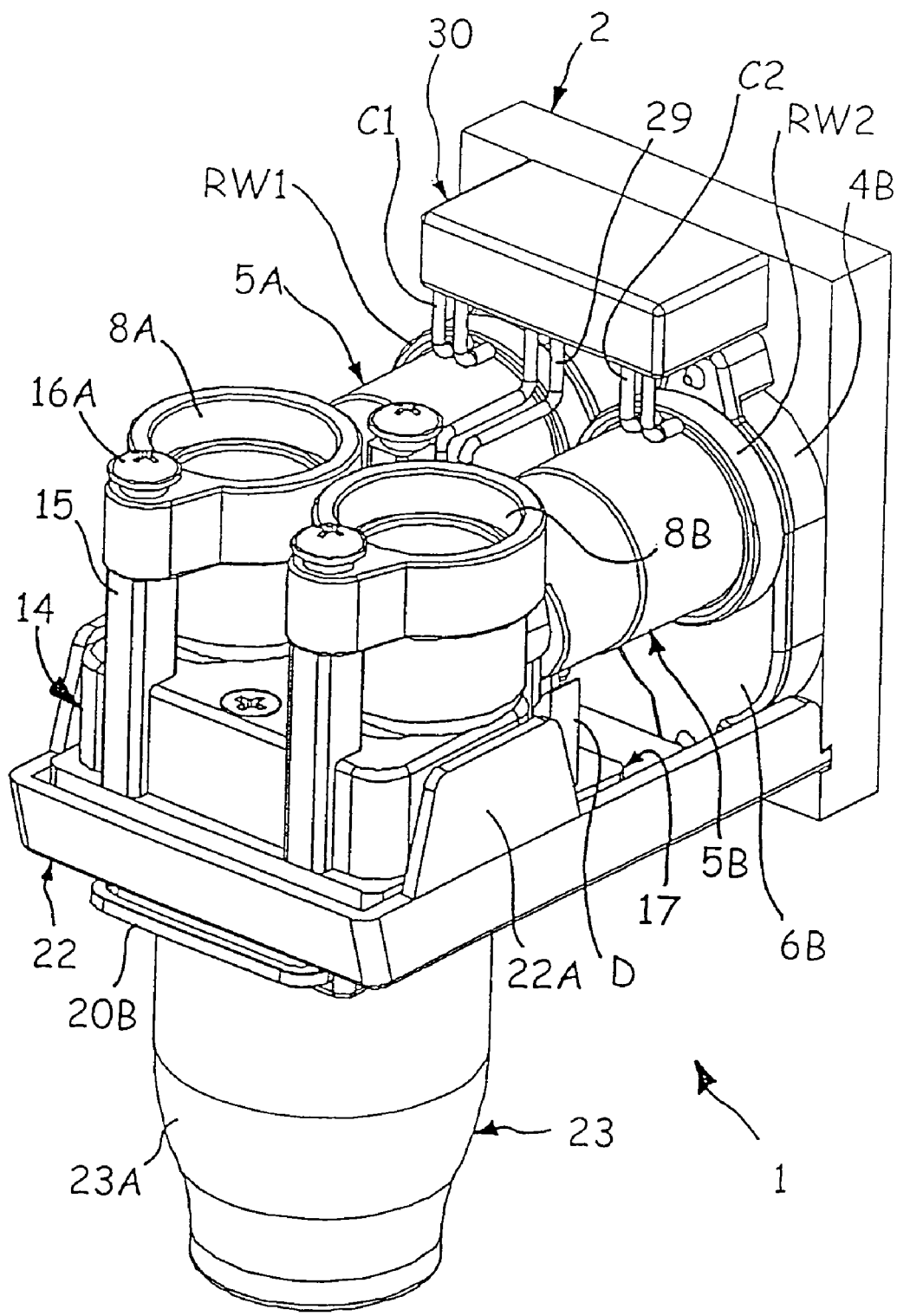
FIG. 1 is a perspective view of a part of a device carried out according to the invention.
Figure 2:
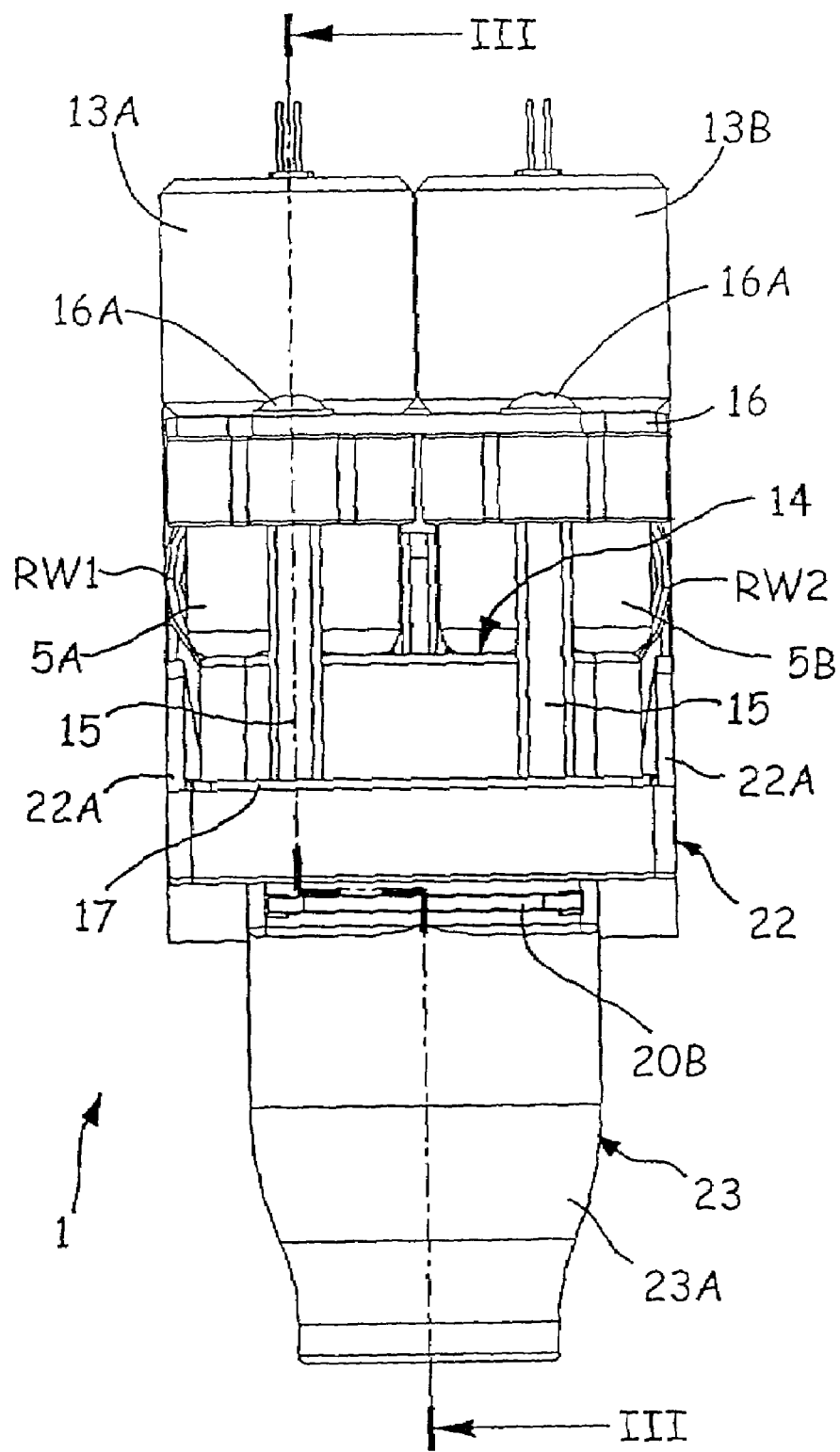
FIG. 2 is a front view of a device carried out according to the invention.

The accompanying figures show a possible practical embodiment of the device 1; note that FIG. 1 does not show for reasons of clarity two actuators (13A, 13B) that are part of the device and can however be seen in the other figures.

The device 1 comprises an interconnection element 2, shaped like a plate, designed for a rapid coupling with a drink vending machine (which can partly be seen in AD in FIGS. 9–11); the interconnection element 2 can be carried out with known techniques, so as to enable a fast mechanical and/or hydraulic and/or electric connection of the device 1 to its corresponding vendor.

Figure 3:
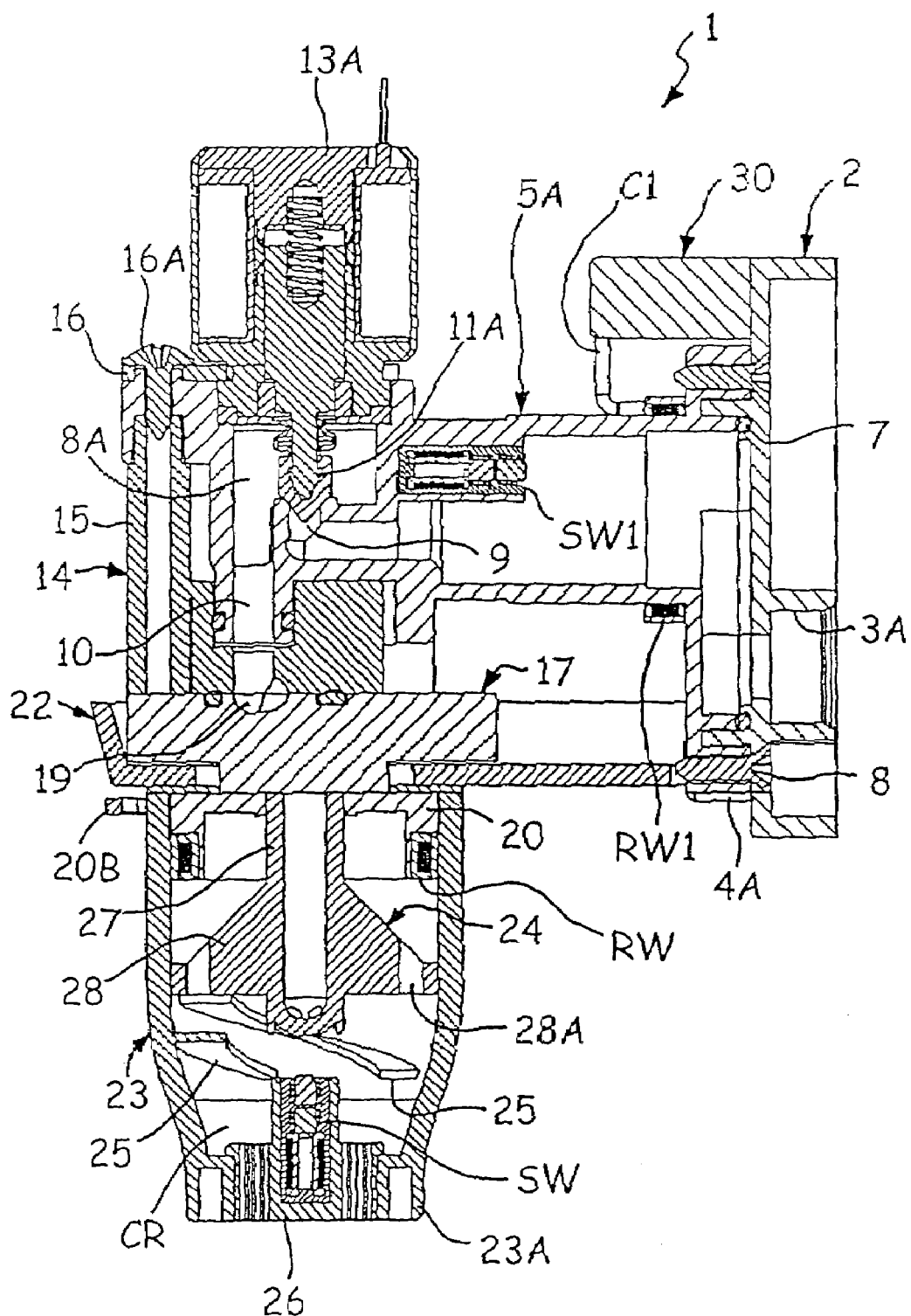
FIG. 3 is a sectional view according to line III—III of FIG. 2.

The interconnection element 2 defines two passages, each designed to be connected to a source of a liquid ingredient, which is supposed to be here either water or syrup; said passages end up in the inner part of the interconnection element 2 into corresponding connection fittings, one of which is referred to with 3B in FIG. 3. As can be seen, in particular in FIGS. 1 and 4, the opposite part of the interconnection element 2 defines two connecting portions 4A, 4B, for corresponding end portions 6A, 6B of two valve bodies, referred to with 5A and 5B, basically parallel to one another and defining a corresponding inner duct. The coupling end portions 6A, 6B of each valve body 5A, 5B are designed to be fitted onto the corresponding portions 4A, 4B of the interconnection element 2, with the interposition of a corresponding sealing washer (one can be seen in 7, FIG. 3); the fastening between the parts is carried out by means of screws, referred to with 8 in FIG. 3.

As can be seen in FIGS. 1 and 3, each valve body 5A, 5B also defines a chamber 8A, 8B housing a corresponding actuating group. Each chamber 8A, 8B, which in this example is open upwards, has an inlet and an outlet, referred to with 9 and 10 in FIG. 3, which are part of the aforesaid duct within the valve bodies 5A, 5B. Each chamber 8A, 8B is designed to house a corresponding shutter 11A (see FIG. 3) and 11B (see FIG. 4), actuated by means of a corresponding position-controllable actuator 13A, 13B, in particular a proportional electromagnet, arranged above the corresponding chamber 8A, 8B.

The outlet 10 of each valve body 5A, 5B is fitted sealingly into a corresponding passage 14A; 14B (FIG. 3) defined in a hooking element 14, basically cap-shaped, from which uprights 15 and hooking teeth D rise, the latter being designed to couple elastically with projections defined on the sides of the two valve bodies 5A, 5B. The numeral 16 refers to a bracket, secured by means of screws 16A onto the ends of the uprights 15 of the hooking element 14, so as to keep the electromagnets 13A, 13B in position.

Figure 4:
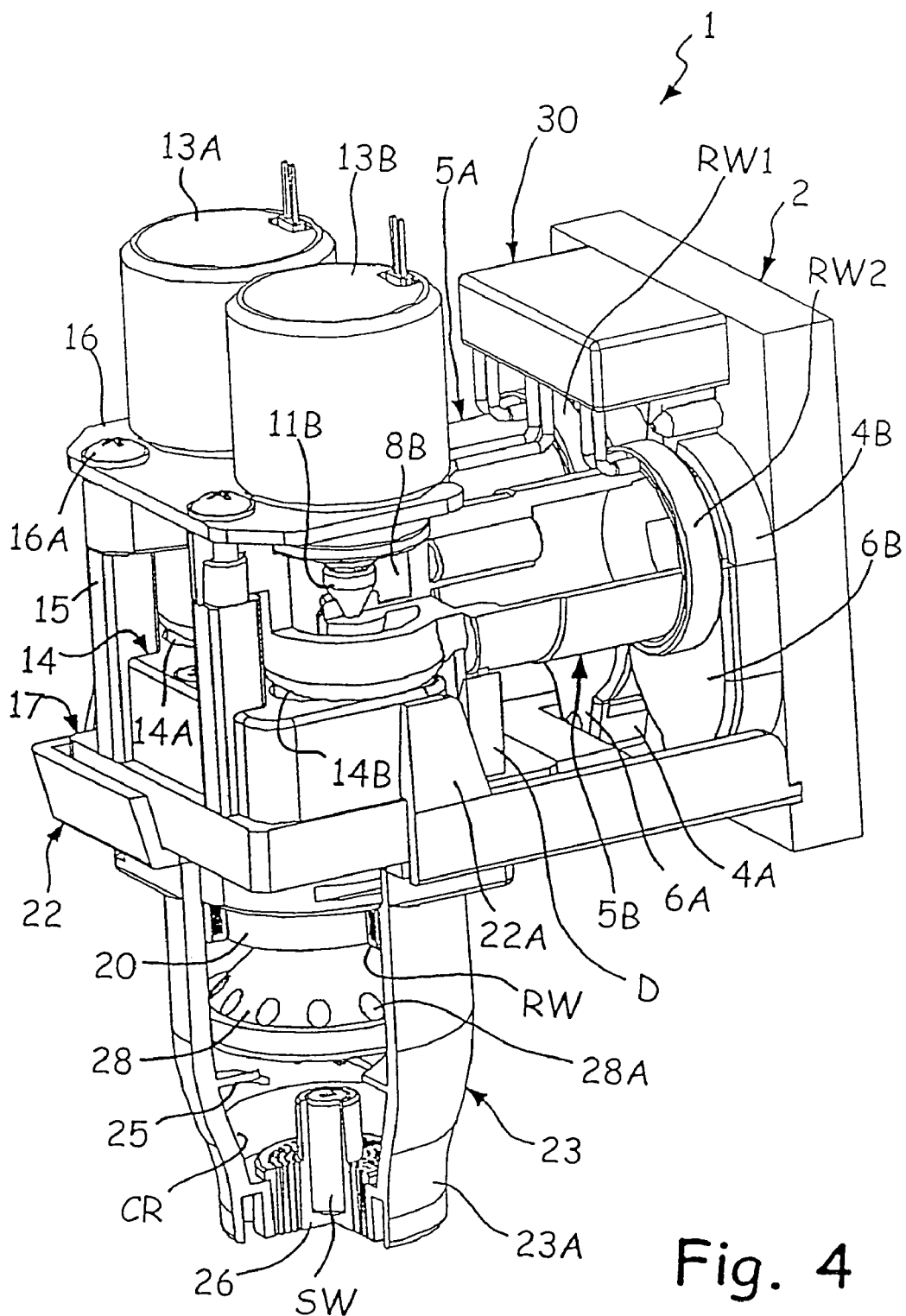
FIG. 4 is a perspective view, partially sectioned, of a device carried out according to the invention.

The hooking element 14 is fitted onto an underlying manifold 17 and fastened to the latter by means of screws (one of them is referred to with 14C in FIG. 1), with the interposition of a suitable sealing washer, which is not visible; the manifold 17 contains two chambers (one can partially be seen in 19, FIG. 3), which—referring to the exemplifying drawings—are open upwards, in the area where the outlets 10 of the two valve bodies 5A, 5B end up; said chambers 19 basically convey water coming from the outlet 10 of the body 5A and syrup coming from the outlet 10 of the body 5B into corresponding outlets, not visible in the figures, which get in their turn, though being two separate ducts, into a common outlet body of the manifold 17, referred to with 20 in FIGS. 3 and 4. The outlet body 20 is fitted into a passage getting through a lower plate 22, hooked by means of elastic fins 22A to the manifold 17 and arranged perpendicularly with respect to the interconnection element 2. The outlet body 20 is hooked to a supply nozzle, referred to with 23, for instance by means of a U-plug, referred to with 20B; the nozzle 23 can be moved or removed, for instance to cleaning purposes.

The nozzle 23 contains inside a static mixer, carried out in a per se known way; in the exemplified case, as can be seen in FIGS. 3 and 4, said mixer comprises an inner diffusing element 24, an outer body 23A containing a series of helical fins 25, and a pierced lower diffuser 26. As can be seen in particular in FIG. 3, the inner diffusing element 24 has a hollow cylindrical upper portion 27 and a basically conical lower portion 28, having a series of passages 28A; the upper end of the portion 27 is fitted into a corresponding seating defined in the outlet body 20 of the manifold 17, on the outlet of the chamber 19 of the manifold 17 through which syrup passes; conversely, the outlet 19 of the manifold 17 through which water passes is placed laterally with respect to the cylindrical portion 27; the lower end of the cylindrical portion is basically shaped as a hemispherical nozzle having a series of radial holes.

The presence of the lower diffuser 26 at the lower end of the nozzle 23 results in the formation within the nozzle of a chamber, referred to with CR in FIGS. 3 and 4, between said diffuser 26 and the inner diffuser 24; in said chamber CR, during supply, a temporary stagnation of liquid can form, i.e. of the mixture consisting of water and syrup. SW refers to a detector of at least a chemical-physical property of the mixture passing through the chamber CR. In the exemplified case the detector is housed in a seating centrally defined in the lower diffuser 26.

According to an important feature of the present invention, the detector SW is designed to carry out a wireless data transmission, i.e. by means of a wireless connection, to a corresponding reader, referred to in the figure with RW. In the exemplified case the reader RW has a ring-shaped watertight body CA and is mounted onto the outlet body 20 of the manifold 17, and therefore, though being mounted directly within the nozzle 23, is integral with the main body of the device, i.e. to parts that are not disassembled to maintenance purposes. In the non-limiting example provided here, the reader RW is practically in contact with the liquid to be measured, but in particularly advantageous solutions said reader could be covered completely by the material of at least a part of the body of the device 1; in said configuration it is convenient to use suitable materials, i.e. not interfering with a wireless transmission, such as for instance thermoplastic materials. The reader RW is connected through corresponding wires 29 to an electric connector and/or to an electronic control circuit, referred to with 30, integral with the interconnection element 2.

Figures 5, 6, 7:
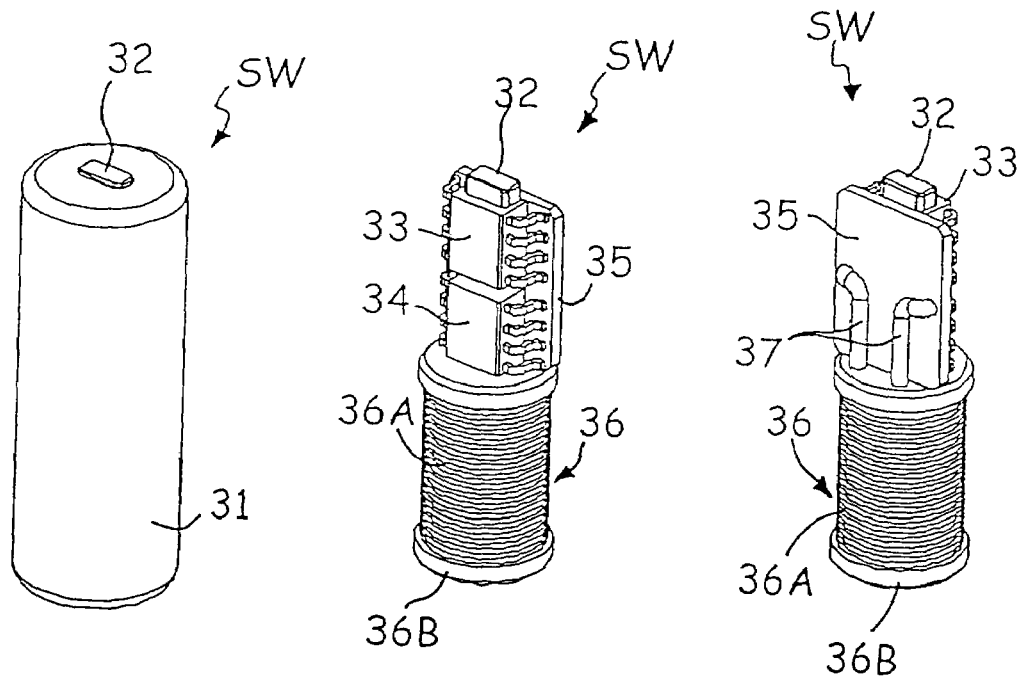
FIG. 5 is a perspective view of a detector used in the device of FIGS. 1–4.
FIGS. 6 and 7 are perspective views, from different angles, of the inner part of the device of FIG. 5.
Figure 8:
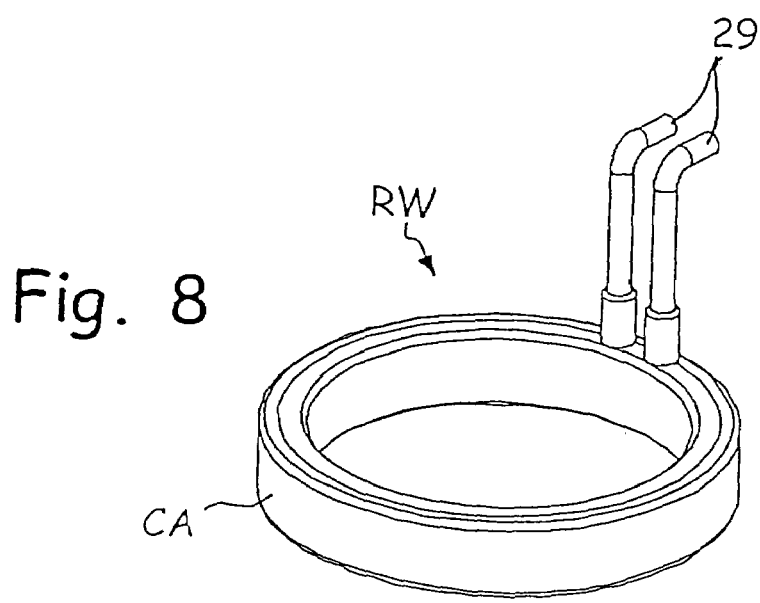
FIG. 8 is a perspective view of a signal receiver used in the device of FIGS. 1–4 together with the detector of FIG. 5.

The detector SW is shown from different point of view in FIGS. 5–7, whereas the reader RW is shown in FIG. 8; by way of example, the system for exchanging information between the components SW and RW can be a radio-frequency system, known as "RF", and in this light the reader RW is the so-called main antenna of the RF transmission system.

The detector SW has an envelope 31, which in the exemplified case has a substantially cylindrical shape and small size, for instance a length of 15–20 mm and a diameter of 6–10 mm. The numeral 32 refers to a sensor element or detection stage of a relevant chemical-physical quantity, which partially projects from an end of the envelope 31. Suppose that in the exemplified case the relevant quantity measured by the device SW is the acidity and/or basicity of the supplied mixture. The acidity of a liquid is conventionally expressed as pH, i.e. "negative logarithm of the concentration of $H^+$ ions", which in aqueous solvents varies for the most commons solutions from 0, corresponding to a strong acidity, to 14, corresponding to a strong alkalinity or basicity.

The dilution of a strongly acid compound (for instance with pH=2) involves a sensible variation of the pH of the resulting mixture (for instance a 10-times dilution with pure water would result in a solution with pH=3); according to this principle, the pH value resulting from the mixing operating is therefore related both to the pH of the concentrated fluid (in the practical example syrup) and to the pH of the diluting fluid (in the practical example water), and above all to the volumes of the two fluids taken into consideration.

The use of pH as operating parameter in the application described here presupposes that the pH of the mixture components, i.e. water and syrup, is known. In a possible embodiment of the invention said pH values can be obtained previously through conventional empirical or experimental analyses, and then be stored in memory means within the control system of the device 1, preferably electronic memory means. Moreover, in a possible advantageous embodiment of the invention, the pH values of the mixture components can be measured directly through two further pH sensors operating inside the ducts through which water and syrup pass, respectively. Anyhow, by measuring the pH of the mixture by means of a suitable sensor, and previously knowing or measuring the pH of its components, it is possible to carry out a convenient adjustment of water and syrup volumes by acting upon their respective adjustment valves. In this light, according to the invention it is possible to define a characteristic pH value of the mixture to be obtained, consisting of correct volumes of its liquid components, as a function of the pH of the syrup and water to be mixed and of their respective temperatures.

A measurement of the pH of the final mixture giving rise to anomalous values will then be interpreted by the control system of the device as due to a mistake in the proportions of the volumes of water and syrup that have been mixed, and the system will automatically correct the supplied volumes of liquid components according to the parameters previously defined in the managing program. In practice, therefore, the method for controlling the quality of the mixing operation according to the invention, implemented by the device 1 in FIG. 1, can include the following steps or basic operations:

i) determination (i.e. measurement and/or predefinition) of the pH value of a first and second liquid ingredient (i.e. water and syrup) used for obtaining a mixture (i.e. the drink in the exemplified case);

ii) determination (i.e. measurement and/or predefinition) of a reference pH value or a range of reference pH values of the mixture to be obtained, the reference value or range of reference values representing the desired quality or property of the mixture;

iii) addition of the first ingredient, with the control of its flow rate and/or amount, by means of at least a first valve;

iv) addition of the second ingredient, with the control of its flow rate and/or amount, by means of at least a second valve;

v) mixing of the first and second ingredient so as to obtain the mixture and supply it;

vi) measurement of the pH value of said mixture, preferably in an area close to the supply and/or mixing area;

vii) processing of the pH value of the mixture as measured, in particular by comparing it with the corresponding reference value or range of reference values; and viii) in case of deviation of the pH value as detected from the reference value or values, adjustment of one or both valves supplying the first and second ingredient, so as to correct the composition of the mixture, so that its pH corresponds to the reference value or falls within the range of reference values.

As previously explained, by measuring the pH of the mixture by means of a suitable sensor and knowing the pH of the two ingredients it is possible to adjust the volumes of the latter by acting upon their respective adjustment valves, so as to obtain a mixture having the desired pH value, which is an indication of the desired quality of the mixture. The aforesaid adjustment can be carried out through processing techniques known per se, for instance using table methods or fuzzy logic. In a first embodiment of the method of pH values of the first and second liquid ingredient (step i), as well as the reference value or values for the mixture (step ii) can be previously calculated by means of experimental analyses and stored in the control logic supervising the operation of the mixing device 1; conversely, the pH value in the supplied mixture (step vi) will be detected directly through a corresponding sensor. In a second embodiment of the method according to the invention also the pH values of the first and second liquid ingredient (step i) can be detected directly through corresponding sensors.

Going back to FIGS. 5–7, the pH sensor 32 can be a commercially available ISFET solid state sensor. It should be noted that, advantageously, such as ISFET meter integrates directly also detecting means for liquid temperature beyond pH. In the exemplified case the sensor 32 is associated to a corresponding measuring circuit 33 and the latter is associated to a data reception/transmission circuit, referred to with 34. The components 33 and 34 are miniaturized integrated circuits, mounted onto a printed circuit 35 to which a miniaturized antenna 36 is fastened, comprising for instance a coil carried out by winding up turns of enameled wire 36A onto a ferrite core 36B. The envelope 31, which can be for instance a resin, coats completely the aforesaid components, but for a portion of the sensor 32, which detects pH and temperature. The transmission/reception circuit 35, to which the measuring circuit 33 is connected, is connected to the antenna 36 through wires 37 that are present in the portion of the printed circuit 35 opposite the one onto which the components 33 and 34 are mounted.

The principle of data transmission/reception between the detector SW and the reader RW can be analogous to the one of radio-frequency passive electric devices without independent power supply or radio-frequency identifiers (also known as RFID, transponder, trasponder or Tag), for instance those that are now commonly present in car keys.

Said radio-frequency devices are known per se and do not require a detailed description here. Let us only remind that a passive transponder is an electric device carrying data and without battery, which reacts to a specific inductive electromagnetic field generated by a corresponding reader replying with a modulated radio-frequency representing data; since no inner energy source is present, passive transponders get their power supply from said electromagnetic field generated by the reader. By mere way of example of the working of transponders, suppose that the circuit 34 is carried out with an integrated module HITAG2 manufactured by Phillips, connected to a known LC circuit (inductance-capacity), integrated into the printed circuit 35 and not shown in the figure, which is designed to be resonant at a given frequency, here 125 KHz.

The supply voltage of the circuit 34 is provided by the reader RW, which acts by generating in a known way a constant electromagnetic field at 125 KHz; in practice, the voltage thus induced onto the aforesaid resonant LC circuit is used as power supply for the integrated circuit 34. The transmission of data between the integrated circuit 34 and the corresponding reader RW takes place by supplying the second element, so that it generates the aforesaid electromagnetic field; this gives rise to a different energy absorption by the circuit 34, which results in a subsequent variation on the antenna built by the reader RW; the circuit 30, by de-modulating said slight variation, obtains the decoding of the transmitted datum, which in this specific case is the result of pH measurement, carried out through the sensor 32.

In other words, therefore, the main antenna RW, operating almost as primary winding of a transformer without yoke, transmits energy to the antenna 36 of the sensor, which could almost be regarded as the secondary winding of a transformer; said energy emission commonly takes place at quite a high frequency (for instance hundreds of KHz or some MHz). The circuit 34 receives and stores, for instance through a small condenser, the energy transmitted to it until it reaches a convenient charge and/or a convenient voltage value; now the electronic circuit 34 supplies the measuring circuitry 32, 33 and the information transmission circuitry. In such conditions the antenna 36 of the detector SW operates as transmitter, whereas the main antenna RW operates as receiving element; during said step, obviously, also the main antenna RW could transmit data to the detector SW, such as for instance a different measurement configuration to be carried out by the sensor 32 and by the corresponding circuit 33.

The detector SW is fitted into the corresponding seating of the diffuser 26, so that the protruding portion of the pH sensor 32 is placed within the chamber CR; on the other hand, as was said, the reader RW is mounted onto the outlet body 20 of the manifold 17 and the device body includes a sealing passage for the wires 29 of the reader RW.

When a drink has to be prepared, the appliance integrating the device 1 acts by mixing a given amount of water and a given amount of syrup. The device 1 is therefore designed to adjust in a known way both the necessary amount of water, let in through the valve body 5A, and the necessary amount of syrup (said metering can take place for instance by means of suitable flow meters or by proportionally adjusting and/or by opening for a given time the intake duct within the valve body 5A, 5B, through the corresponding shutter 11A, 11B).

After a drink request, carried out for instance by manually acting upon an electric switch, the control system of the vending machine on one hand suitably excites the electromagnet 13B; this results in that the shutter 11B protruding into the duct within the valve body 5B is lifted, so as to conveniently open the corresponding inlet 9 leading to the chamber 8B; the syrup then gets into the chamber 8B and flows through the outlet 10 into the corresponding chamber 19 of the manifold 17. The electromagnet 13B is excited in the way and as long as it is deemed as necessary in order to obtain the desired amount of syrup. On the other hand, the control system of the drink vending machine excites basically in the same way also the electromagnet 13A. Thus, the water getting in from the connection 3A reaches the chamber 8A of the valve body 5A through the corresponding inlet 9 not closed by the shutter 11A and then gets out from the outlet 10 within the corresponding chamber 19 of the manifold 17.

Syrup and water can then reach from said chambers 19 the nozzle 23. In particular, water reaches first the area placed above the portion 28 of the inner diffuser 24 and is then conveyed through the passages 28A towards the helical fins 25; conversely, syrup gets into the inner cavity of the cylindrical portion 27 of the inner diffuser 24, on whose bottom it is sent out radially towards the fins 25. The presence of said fins generates a sort of vortex in the water coming from the passages 28A, which makes the mixing between water and syrup within the chamber CR simpler; the mixture or drink can then flow through the holes of the diffuser 26 to be supplied. During said step the control system of the drink vending machine supplies the reader RW, which then supplies in its turn, as previously described, the detector SW; the latter carries out the measurement and transmits the data concerning pH and temperature of the mixture, which are decoded by means of the reception system consisting of the reader RW and of the corresponding circuit 30; the latter then communicates the data to the control system of the drink vending machine.

The pH value thus measured is processed by the control system of the appliance, and in particular compared with a reference value or range of reference values, which indicates the desired quality of the mixture. Should the detected pH value be different from the reference value or values, the position of one or both shutters 11A, 11B will be changed, so as to vary the water and/or syrup flow rate and thus correct the mixture composition until its pH, detected by means of the system detector SW-reader RW, corresponds to the reference value or falls within the range of reference values.

In the operating example described above it can be supposed that the pH values of water and syrup, which are operating parameters required for the volumetric adjustment of said liquids, are pre-stored in the control system of the drink vending machine. Moreover, as was said, in a possible advantageous embodiment of the invention the device 1 can be equipped with detecting means for said chemical-physical property also for the two components of the mixture, i.e. water and syrup.

To this purpose, as can be noted in FIGS. 3 and 4, each valve body 5A, 5B defines a positioning seating for a corresponding detector of the same physical-chemical quantity or quantities measured by the detector SW, i.e. pH in the exemplified case (and possibly temperature). Also in this case, therefore, the detectors SW1 and SW2 are immersed in the liquid to be measured when the latter is introduced into the bodies 5A, 5B. Said further detectors SW1 and SW2 can be analogous to the detector SW, and provided with corresponding readers RW1 and RW2, carried out like the reader RW; the readers RW1 and RW2 are connected to the decoding circuit 30 through corresponding wires C1, C2. In the exemplified case the readers RW1 and RW2 are fitted onto the outside portion of the valve bodies 5A, 5B.

The working of the device 1 in the embodiment comprising both the detector SW1 and the detectors RW1 and RW2 is similar to the one previously described, but for that in this case the pH values of water and syrup are detected directly by the detectors SW1 and SW2 with the corresponding reception and decoding means RW1, RW2 and 30, instead of being pre-stored in the control system of the drink vending machine.

It should further be pointed out that the known methods and devices for controlling the mixing amount, based on measurements of conductivity and refractive index as mentioned in the introduction to the present description, envisage a detection only on the outlet, i.e. on the supplied mixture or drink. Concerning this, however, it should be noted that the chemical-physical properties of the liquid constituents or ingredients (water and syrup) of the drink cannot be regarded as constant in all operating conditions; for instance the electric conductivity of the mixture is strongly affected by water conductivity, which depends in its turn on the features of the water network, and can then vary within a wide range. The same can apply to syrup, whose variations (for instance in its preparation or during its conservation) decidedly affect both conductivity and refractive index and pH, and so on, and jeopardizes the exactness of the measurement. In order to overcome said drawback the invention also envisages another method for controlling the mixing quality, which can also comprise the detection of the chemical-physical properties of the fluids getting into the device, i.e. the following basic operations:

i) pre-definition of a reference value or range of reference values of at least a chemical-physical quantity of a desired fluid mixture (for instance a drink), the reference value or range of reference values representing a desired quality of the desired mixture;

ii) measurement of at least a first value of the chemical-physical quantity (in the example: pH, conductivity, refractive index, sugar percentage, and so on) of a first fluid ingredient to be used for preparing the desired mixture (water in the example);

iii) measurement of at least a first value of the chemical-physical quantity (in the example: pH, conductivity, refractive index, sugar percentage, and so on) of a second fluid ingredient to be used for preparing the desired mixture (syrup in the example);

iv) determination of control and/or adjustment parameters representing the flow rates and/or amounts of the first and second fluid ingredient required to obtain a mixture whose value of the chemical-physical quantity corresponds to the reference value or falls within the range of reference values, the determination of the control parameters being carried out as a function of the reference value or range of reference values and of the first measured values;

v) addition of the first and second ingredient, with the control of their flow rates and/or amounts based on the control parameters determined, and mixing of the first and second ingredient so as to obtain and supply the desired mixture;

vi) measurement of at least a value of the chemical-physical quantity of the supplied mixture;

vii) processing of the measured value of the chemical-physical quantity of the supplied mixture, in particular by comparing it with the corresponding reference value or range of reference values; and viii) in case of unconformity between the measured value of the chemical-physical quantity of the supplied mixture and the reference value or values of the desired mixture, change of said parameters.

In practice, therefore, according to the suggested method each drink that can be obtained from the post-mix vendor is associated to a corresponding reference value of the relevant chemical-physical value, as stored in the control system SC (step i).

Convenient selection means can be advantageously provided for the control system, so as to couple the mixing device according to the invention with the reference values of the drink to which it has been associated.

In the case of post-mix vendors comprising several mixing devices, the control system can comprise the same number of selection devices, which can be configured for instance by the user or by the appliance operator.

After the request for a drink, the control system SC checks the relevant property of water and syrup getting in by means of the sensors 31A and 31B (steps ii and iii); on the basis of the respective values as measured the control system SC calculates the theoretical flow rates of water and syrup required for obtaining an optimal drink, i.e. whose value of the chemical-physical property corresponds to the reference value; water and syrup flow rates are then adjusted and the two ingredients are mixed so as to obtain the drink, which is then supplied (step v).

The value of the relevant quantity of the supplied mixture is measured by means of the sensor 29 (step vi) and compared with the reference value for the desired drink (step vii); said measuring and comparing step is further necessary in order to compensate possible tolerances of the supply system (step viii), for instance positioning tolerances of the shutters 11A, 11B, in order to ensure the highest level of accuracy as possible.

The aforesaid operating steps can be varied or integrated, but for the final aim of optimizing the measurement and/or adjustment of the product or fluid getting out. Concerning this, it should be noted that in practice the properties of one or both products or fluids getting in can be measured continuously, processing again as a consequence new instantaneous reference parameters for the adjustment of the mixture getting out. In other words, the aforesaid parameters can be varied as a function of possible instantaneous variations of the quality of one or both products getting into the device. Said variation of reference parameters is obviously carried out also as a function of said requirements of dose adjustment and/or compensation, for instance so as to compensate previous false adjustments and/or to compensate possible tolerances of the device.

By using the aforesaid selection means it could further be possible to carry out a selection, for instance by the user, of a reference value (step i) among several predefined reference values, so as to obtain different mixing ratios, as desired.

From the above it can be inferred that by measuring the relevant chemical-physical value or values of the mixtures getting out through a suitable sensor, and by measuring through sensors the same value or values of the two ingredients getting in, it is possible to adjust the volumes of the latter by acting upon the corresponding adjustment valves, so as to obtain a mixture having the desired value of the relevant quantity or quantities. Also in this case the adjustment can be carried out using processing techniques known per se, for instance table methods or fuzzy logic.

The chemical-physical quantity or quantities that are relevant for the em-bodiment of the method described above could be different. For instance, the sensors SW, SW1 and SW2 could be pH sensors, as in the previous example, or refractive index sensors or sugar percentage sensors, or pressure sensors, or electric conductivity sensors, and so on. Anyhow, with the method here suggested it is possible to measure the values of the desired quantity or quantities of syrup and water to be mixed, as well as of the mixture consisting of the volumes of the components, in real time, while supply is going on. A measurement giving rise to anomalous values will then be interpreted as due to a mistake in the proportions of the mixed volumes, and the system will automatically correct the supplied volumes according to the parameters predefined in the managing program.

Leaving aside the measured quantity or quantities, in the case of the embodiment described above, the measured value of the chemical-physical values of the mixture will be compared by the control system with a corresponding reference value or with the pre-stored range of reference values. Should the measured value of the relevant value of the mixture be different from the reference value or values, the control system will change the position of one or both shutters 11A, 11B, so as to vary the water and/or syrup flow rate and thus correct the mixture composition until the measured value corresponds to the reference value or falls within the range of reference values. The adjustment of the positioning of the shutters 11A and/or 11B will be here carried out both as a function of the measured value of the chemical-physical of water and/or syrup, and as a function of the reference value or range of reference values of the chemical-physical value of the mixture.

It is evident that the method here suggested can be implemented using the detectors SW, SW1, SW2 together with corresponding reading means RW, RW1, RW2 e decoding means 30.

Figure 9:
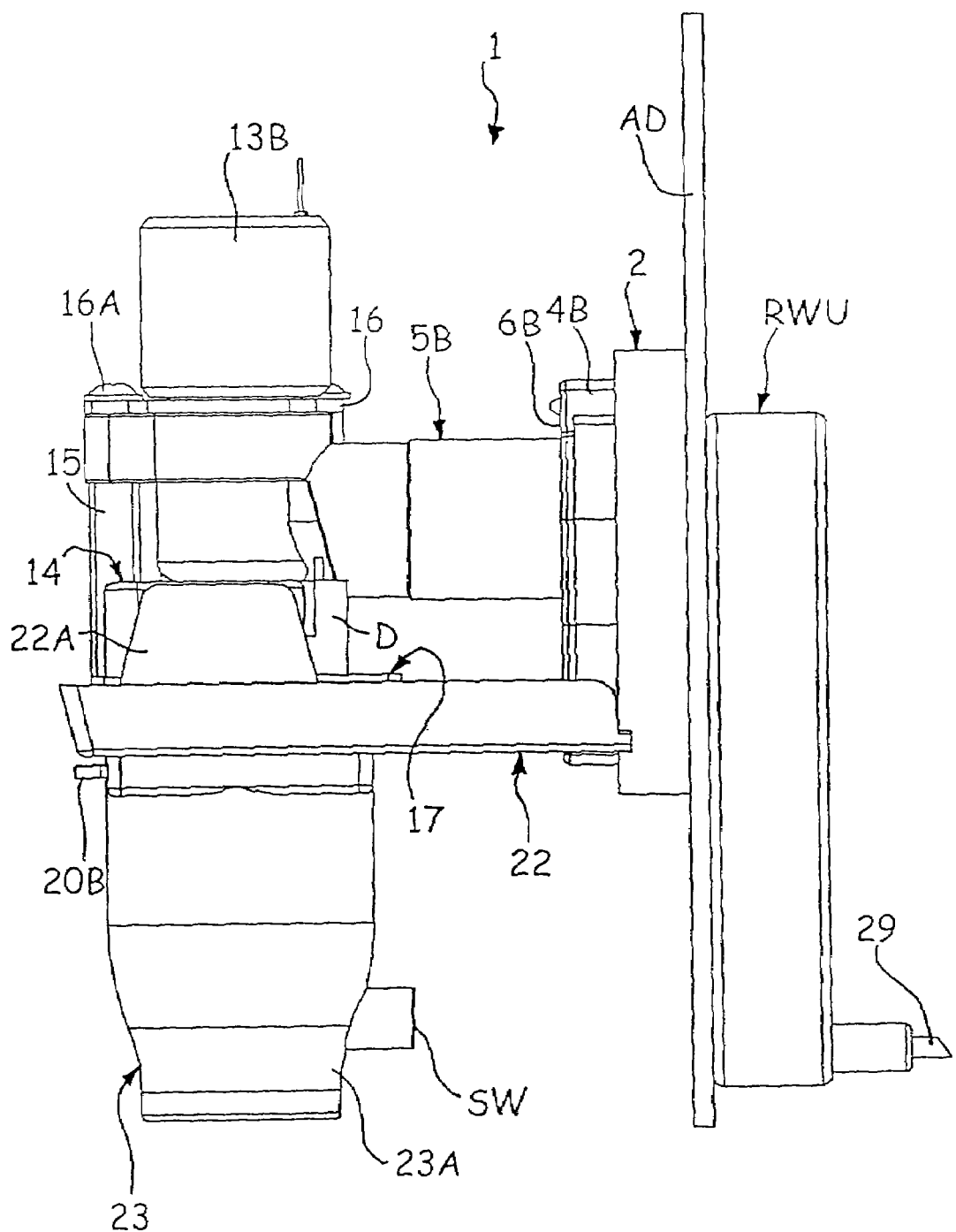
FIG. 9 is a lateral view of a device carried out according to a possible execution variant of the invention.
Figure 10:
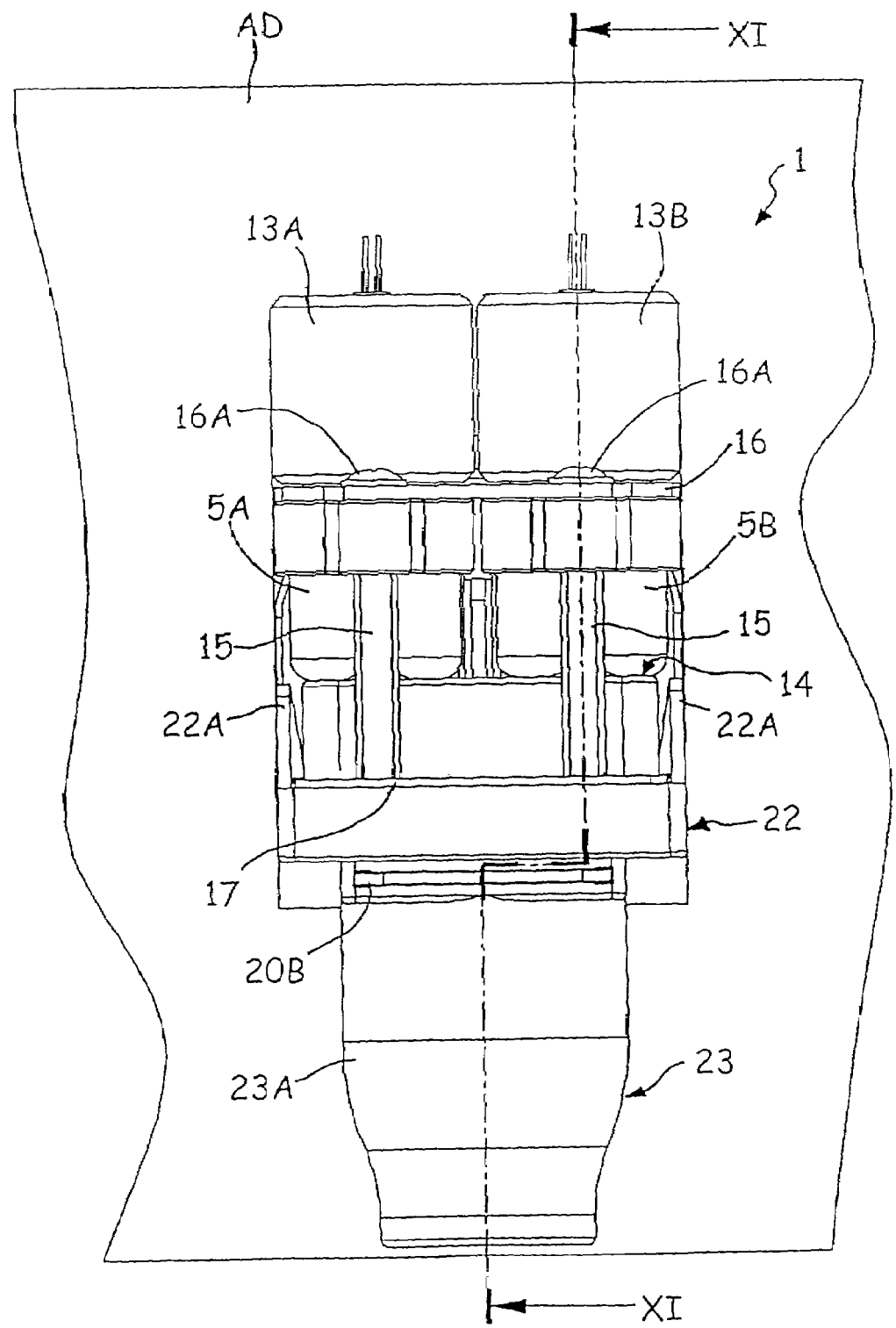
FIG. 10 is a front view of the device of FIG. 9.
Figure 11:
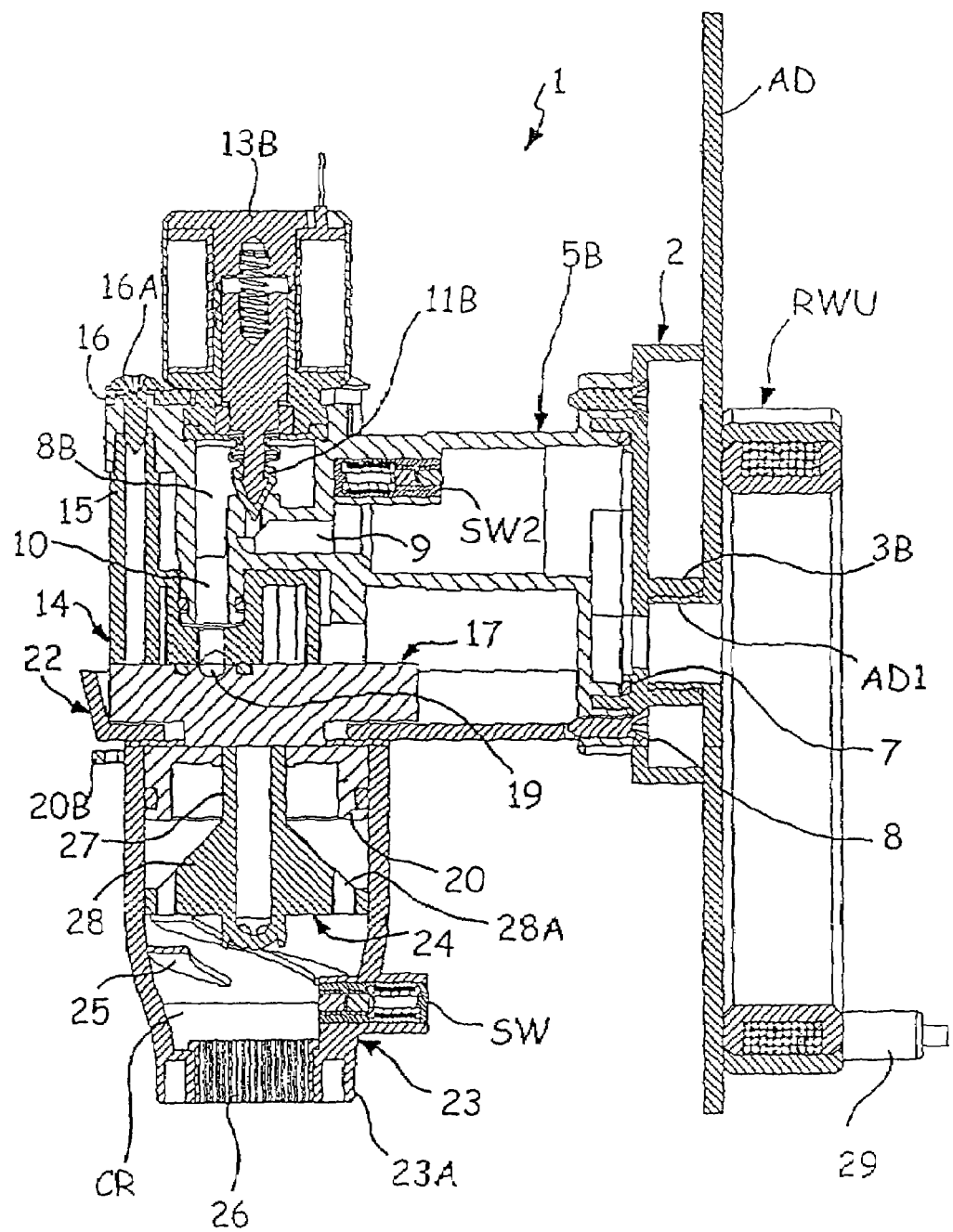
FIG. 11 is a sectioned view according to line XI—XI of FIG. 10.
Figure 12:
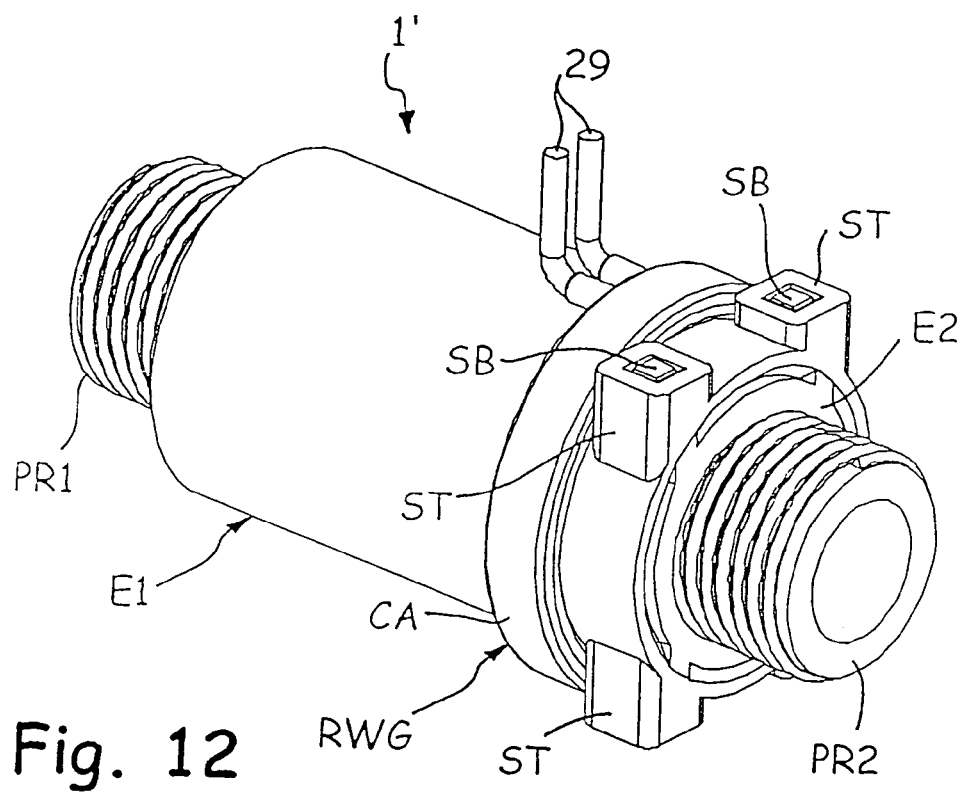
FIG. 12 is a perspective view of a second device carried out according to the invention.

FIGS. 9, 10, 11, where references are the same as in the previous figures, show a possible execution variant of the invention, which envisages one only main antenna or reader for the radio-frequency data transmission system, globally referred to with RWU, which is fastened directly within the drink vending machine, schematically referred to with AD, from whose body project the connections of the ducts coming from the water and syrup supplies (one of said connections is referred to with AD1). Also in this case the reader RWU is equipped with corresponding wires 29 for the connection to a corresponding supply and control circuit, as previously referred to with 30. It should be pointed out that in the case of the variant of FIGS. 9–11, the detectors SW, SW1 and SW2 are preferably oriented towards the main antenna RWU.

In said embodiment the reader RWU with the corresponding control circuit is designed to dialogue selectively with the detectors SW, SW1 and SW2; this can be obtained by envisaging suitable identifying codes for each detector, which the latter sends together with the detection data concerning the detected chemical-physical quantity (similarly to a data "packet" transmission, each packet being identified by means of a univocal code); together with or as an alternative to said technique, the recognition of the origin of the data received from the antenna RWU can be obtained by means of suitable delays in data transmission by the various detectors (for instance: detector SW placed in mixing nozzle 23 transmits first, detector SW1 located in the duct where water flows transmits second, and so on).

As was said, the invention has been described by way of example with particular reference to a mixing device for drink vendors, but it is obvious that the detecting means with wireless data transmission as previously described can also be used in other appliances or devices where hydraulic and/or chemical-physical quantities of a fluid have to be detected. Among these we may quote by mere way of example:

hydraulic devices integrating flow meters, flow rate meters, pressure meters, and so on, for a fluid;

devices for treating liquids, such as softeners or purifiers comprising detecting means for water hardness, detergent dispensers for washing machines, comprising a tank in which means detecting the level and/or presence of a liquid washing agent are located;

washing tanks of washing machines or dishwashers, to which temperature sensors or sensors detecting the degree of conductivity or turbidity of the washing liquid are associated.

With reference to FIGS. 12 to 16, a further practical example of the present invention is provided to this purpose, together with a flow meter or flow rate meter, globally referred to with 1'.

In the exemplified case the meter 1' comprises a body consisting of a first tubular element E1 and of a ferrule-shaped element E2, provided with corresponding threaded connecting portions PR1 and PR2, so as to form a duct P; said connecting portions enable for instance to interpose the device 1' between two ducts 1 conveying a generic fluid whose flow or flow rate has to be measured or checked. By mere way of example, the coupling between the tubular element E1 and the ferrule-shaped element E2, with a suitable sealing gasket GT placed in between, can be carried out by placing two transversal seatings ST on the first element, which seatings are designed to receive each a corresponding locking plug.

Figure 13:
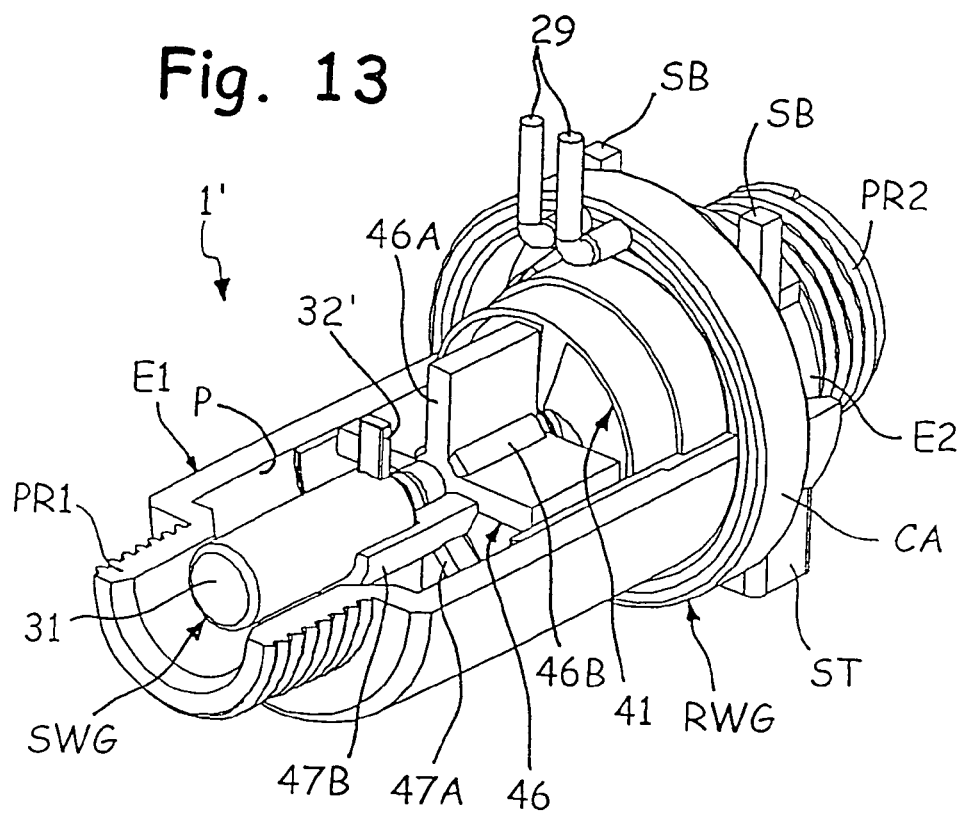
FIG. 13 is a perspective view, partially sectioned, of the device of FIG. 12.
Figure 14:
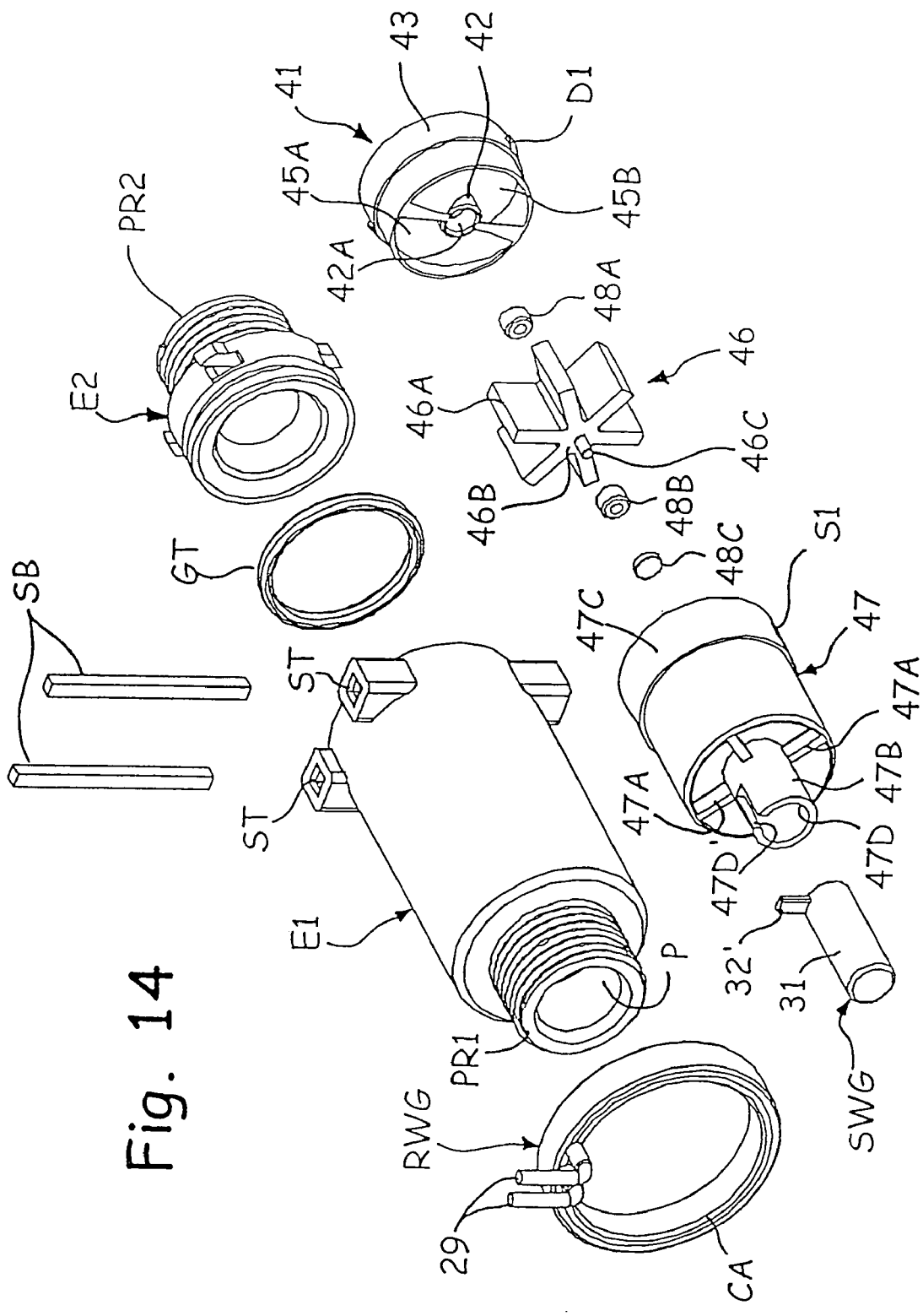
FIG. 14 is an exploded view of the device of FIG. 12.
Figure 15:
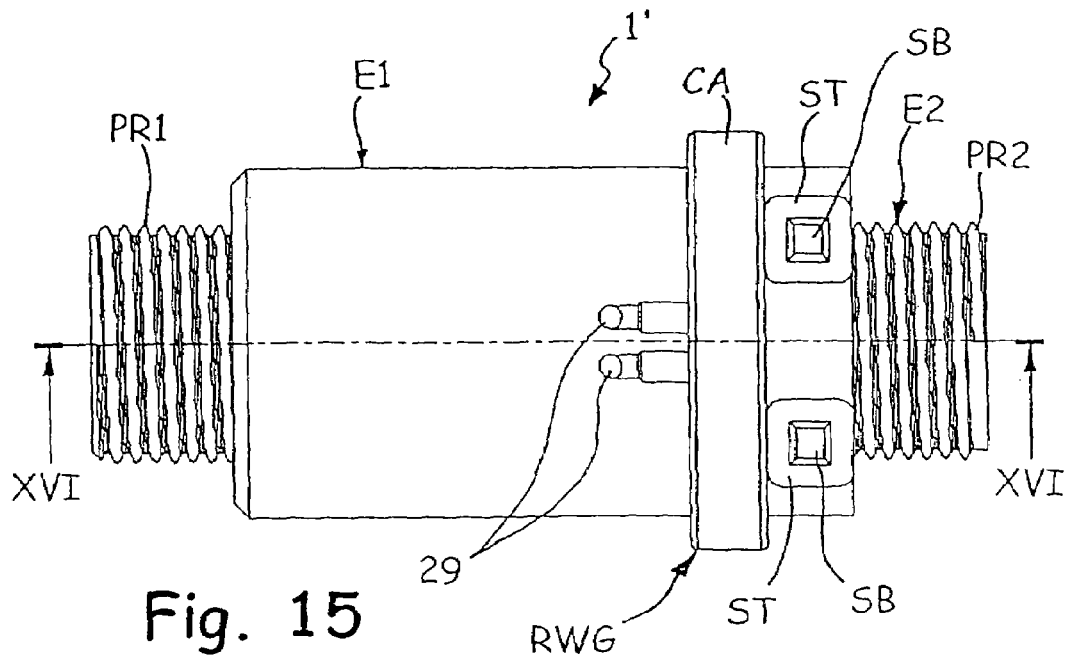
FIG. 15 is a plan view of the device of FIG. 12.
Figure 16:
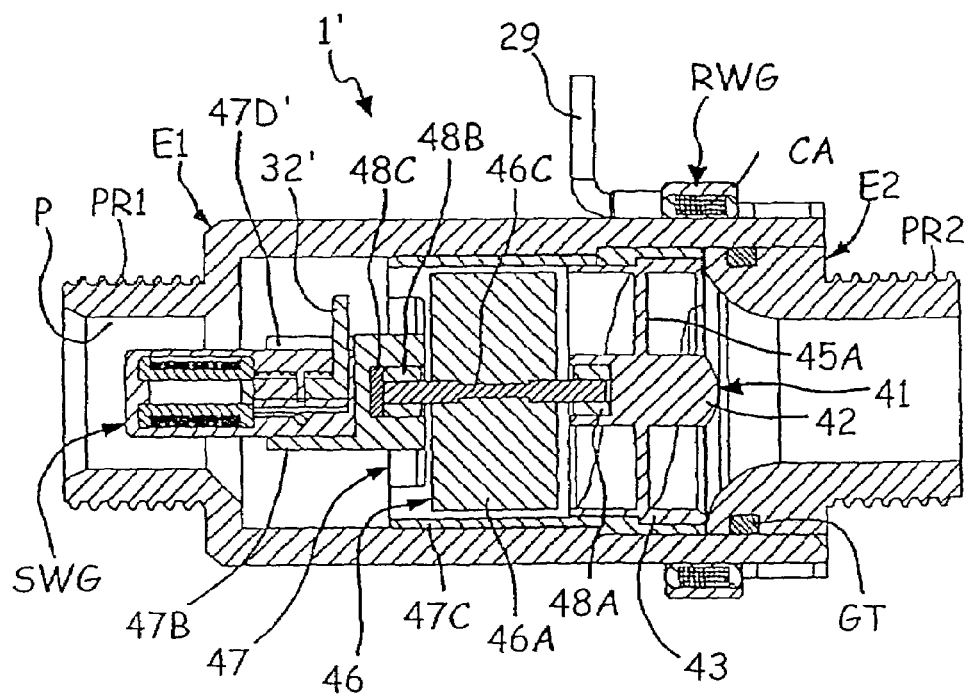
FIG. 16 is a sectioned view according to line XVI—XVI of FIG. 15.

Within the body consisting of the elements E1–E2 a measuring insert is placed, whose components can be seen in detail in FIGS. 13, 14, 16. In said figures the numeral 41 refers to a conveying element, or diffuser, comprising in particular a central core 42 and an outer ring 43, between which at least two helical separators 45A, 45B extend in width direction. As is known from the prior art, the diffuser 41 acts by conveying the water flow onto an underlying impeller, referred to with 46. In the exemplified case the impeller 46 has a body defining a series of blades 46A starting from a core 46B, with which an axial pin 46C is integral; as an alternative to a rectilinear development of the blades 46A, i.e. basically parallel to the pin 46C, said blades could advantageously be inclined or have a helical shape, where the inclination is in the opposite direction with respect to the separators 45A, 45B of the diffuser 41. The impeller 46 is preferably carried out with a compound of barium or strontium ferrite alloyed with a thermoplastic component; said material, also known as platoferrite, is permanently magnetized and therefore preserves to an unlimited extent its magnetic properties if kept within a temperature range between −20 and +70° C. The blades 46A of the impeller 46 are then associated to magnetic polarities, whose aim is to induce an electric signal in a convenient magnetic sensor (in the following referred to with 32').

The numeral 47 refers to a cylindrical envelope, open on its upper end and having on its lower end a series of support elements or spokes 47A, which extends radially from a central core 47B on the cylindrical wall 47C of said envelope, as can be seen for instance in FIG. 13 or 14. The diffuser 41 and the envelope 47 are shaped so as to fit one into the other by means of reciprocal hooking means, so as to form the aforesaid insert or component comprising the impeller 46; the aforesaid hooking means consist, in the case shown in FIG. 13, of teeth D1 on the outer surface of the ring 43 of the element 41, which can elastically engage into corresponding seatings S1 defined in the upper portion of the envelope 47.

The part comprising the core 42 of the diffuser 41 defines a seating, referred to with 42A in FIG. 13, housing a bushing 48A supporting the pin 46C of the impeller 46 (as can be seen in FIG. 16); a similar bushing, referred to with 48B, is placed on a first seating defined within the core 47B of the envelope 47 (see FIG. 16); in said first seating, below the bushing 48B, a thrust bearing 48C for the pin 46C of the impeller 46 is arranged.

The bushings 42A, 48B and the disk 48C are preferably carried out in a material having a low friction coefficient and a high resistance to wear and tear (chosen for instance among bronze, graphite, hard stones and/or materials having similar features suitable to this purpose). The envelope 47 and the diffuser 41 can be carried out in thermoplastic material with molding operations; the same applies to the magnetically active portion of the impeller 46, to which the axial pin 46C is associated; the bushings 48A, 48B and the thrust bearing 48C are commercially available components.

The core 47B of the envelope 47 also defines a second seating, opposite the previous one, referred to with 47D in FIG. 14, having a basically tubular shape and having a longitudinal slit 47D'. Said second seating 47D is designed to house a detector of the turns of the impeller 46, referred to with SWG; the detector SWG is substantially carried out according to the technique previously described with reference to detectors SW, SW1 and SW2 of the device 1 of FIGS. 1–11.

In this case, instead of a sensor of a chemical-physical property of the fluid, the detector SWG comprises a magnetic sensor 32', which protrudes laterally from the outer envelope 31 of said detector; the detector SWG is fitted into the corresponding seating 47D of the core 47B, with the sensor 32' fitted into the slit 47D' protruding outside from the latter, so as to detect the passage of the magnetic blades 46A of the impeller 46.

Also the embodiment of FIGS. 12–16 envisages outside the body consisting of the elements E1–E2 a reader RWG, similar to the detectors RW, RW1 and RW2, equipped with corresponding wires 29 connected to a corresponding supply and control circuit, analogous to the one previously referred to with 30.

The device 1' works as follows.

The fluid or liquid penetrates into the body of the device 1' through the duct within the ferrule-shaped element E1; the liquid is thus conveyed by means of the separators 45A, 45B onto the blades 46A of the impeller 46; the impeller 46 is then put into angular motion by the flow of liquid flowing out, which can get out of the device through the connecting portion PR1 of the element E1. In said step the control system of the device 1' supplies the reader RWG, which subsequently supplies in its turn, as previously described, the detector SWG. The rotation of the impeller 46 is thus detected by the magnetic sensor 32' thanks to the fact that the impeller is made of magnetic material; the detections received by the sensor 32' can be for instance processed on the spot by a suitable measuring circuit (positioned as circuit 33 in FIG. 6), whose output data are decoded by means of the reception system consisting of the reader RWG and of the corresponding supply and decoding circuit.

The insert or component resulting from the coupling between the envelope 47 and the diffuser 41, with the impeller 46 placed in between, can be introduced directly into a duct that is part of another device; in this light, for instance, it should be pointed out that the insert 41–47 could be fitted into one of the ducts within the bodies 5A, 5B of a mixing device as described with reference to FIGS. 1–11; in said embodiment the detector reader RWG will be fastened in a position similar to that of the detectors readers RW1 or RW2.

The flow meter 1' is particularly advantageous in post-mix dispensers thanks to its small size and to the fact that the aforesaid insert 40 can be fitted directly into the duct for the addition of the liquid to be measured. Said features, beyond resulting in the reduction of the overall size of the electric valve 1, prevent the need for specific fastening and holding means, which are typical of tangential flow meters used until today to this purpose in post-mix dispensers. Also assembling operations for the electric valve 1 are simpler and faster.

Obviously, though the principles of the invention remain the same, construction details and materials and embodiments can be widely changed with respect to what has been described and disclosed.

With reference to the embodiment of FIGS. 12–16 it should be pointed out that the rotation of the impeller 46 can be detected with a system other than the magnetic one, such as for instance an optical detection system, which is widely used in the field of flow meters.

Among the other variants of the invention it should be pointed out that there could be an operating stage enabling also the possible correction of the mixture portion already supplied, calculating and supplying a following "compensation" mixture portion directly into the glass; said variant is quite easy to be carried out with reference to the application and method described above based on the presence of detecting means for a property both of the mixture components and of the mixture itself. For instance, in the initial supply step, while the first measurements of the relevant properties and/or the first correction of the adjustments are being carried out, a mixture with too much syrup could be supplied; in such a case, having measured in a known way the flow rate of at least one of the supplied liquids (for instance water, by means of a device like the one in FIGS. 12–16, connected upstream from the body 5A), it is possible to calculate and supply a further mixture with less syrup, so that the latter gets mixed in the glass with the one containing too much syrup, thus obtaining an optimal average value.

What is claimed is:

1. A device comprising
 a body in which a space is defined for containing or allowing passage of a fluid,
 first detecting means for at least a hydraulic or chemical and/or physical property of the fluid contained in or passing through said space,
 a control system, connecting means for connecting said first detecting means with said control system,
wherein said connecting means comprise
a radio-frequency passive electric circuit without independent power supply, connected to said first detecting means and
receiving means interfaced to said control system,
and wherein said passive circuit is operative for transmitting data by radio-frequency to said receiving means.

2. The device according to claim 1, wherein said passive circuit and at least a part of said first detecting means are housed in a same envelope.

3. The device according to claim 2, wherein said envelope is housed within said body and said receiving means are arranged outside said body.

4. The device according to claim 2, wherein said envelope is pro-vided for being immersed in said fluid.

5. The device according to claim 1, wherein said receiving means comprise a respective circuit for supplying and decoding data transmitted by radio-frequency.

6. The device according to claim 1, wherein said first detecting means comprise a sensor, in particular a solid state sensor.

7. The device according to claim 6, wherein said first detecting means comprise a measuring circuit connected to said sensor.

8. The device according to claim 1, wherein said passive circuit comprises at least a miniaturized integrated circuit.

9. The device according to claim 1, wherein said passive circuit comprises a miniaturized antenna.

10. The device according to claim 1, wherein said receiving means is operative for transmitting data by radio-frequency to said passive circuit.

11. The device according to claim 7, wherein said receiving means are operative for transmitting by radio-frequency to said passive circuit configuration data for said measuring circuit.

12. The device according to claim 1, wherein said first detecting means are designed to detect one or more properties of the fluid, chosen in the group consisting of pH, refractive index, sugar percentage, pressure, electric conductivity, temperature, flow, flow rate, amount, level.

13. The device according to claim 1, characterized in that second detecting means are provided.

14. The device according to claim 13, characterized in that said second detecting means have corresponding connecting means comprising
a respective radio-frequency passive electric circuit without in-dependent power supply, and
respective receiving means interfaced to said control system,
and wherein each passive circuit is operative for transmitting data by radio-frequency to the respective receiving means.

15. The device according to claim 13, characterized in that said first and second detecting means have common connecting means to said control system, said common connecting means comprising
a radio-frequency passive electric circuit without independent power supply for each of the detecting means provided for, and
common receiving means interfaced to said control system,
where each passive circuit is operative for transmitting data by wireless radio-frequency to said common receiving means.

16. The device according to claim 15, wherein said common receiving means are operative for identifying selectively data transmitted by the first and second detecting means.

17. The device according to claim 1, wherein it is a device for treating a liquid, such as a decalcifying device.

18. The device according to claim 1, wherein it is a dispenser of washing agents for washing machines, comprising a tank, said first detecting means being provided for detecting at least one of the level and the presence of a liquid washing agent in the tank.

19. The device according to claim 1, wherein it is the washing tank of on of a washing machine or a dishwasher.

20. A device for preparing a mixture of liquids, in particular a drink, comprising:
a first duct for the addition of a first ingredient, on which acts a first element for adjusting a flow rate thereof,
a second duct for the addition of a second ingredient, on which acts a second element for adjusting a flow rate thereof,
a mixing area of the first ingredient with the second ingredient, so as to obtain said mixture, the mixing area being downstream from said first duct and said second duct,
control means operative for controlling the first element for adjusting and the second element for adjusting,
first detecting means for at least a hydraulic or chemical and/or physical quantity of at least one of the first ingredient, the second ingredient, the mixture to be obtained,
connecting means for connecting said first detecting means to said control system means,
wherein said connecting means comprise
a wireless data transmission circuit, connected to said first detecting means, and
a receiving circuit for said data interface to said control means.

21. The device according to claim 20, wherein said transmission circuit and at least a part of said first detecting means are housed in a same envelope.

22. The device according to claim 21, wherein said envelope is housed within said mixing area.

23. The device according to claim 22, wherein said envelope is provided for being immersed in said mixture.

24. The device according to claim 20, wherein said first detecting means comprise a solid state sensor.

25. The device according to claim 24, wherein said first detecting means comprise a measuring circuit connected to said sensor.

26. The device according to claim 20, wherein said transmission circuit comprises a miniaturized integrated circuit.

27. The device according to claim 20, wherein said transmission circuit comprises a miniaturized antenna.

28. The device according to claim 20, wherein said receiving circuit is operative for transmitting data by radio-frequency to said transmission circuit.

29. The device according to claim 25, wherein said receiving circuit is operative for transmitting by radio-frequency to said transmission circuit configuration data for said measuring circuit.

30. The device according to claim 20, wherein said first detecting means are provided to detect one or more properties of the mixture, chosen in the group consisting of pH, refractive index, sugar percentage, pressure, electric conductivity, temperature, flow, flow rate, amount, level.

31. The device according to claim 20, wherein said transmission circuit comprises a radio-frequency passive electric circuit without independent power supply.

32. The device according to claim 31, wherein said receiving circuit comprises means for supplying and decoding data transmitted by radio-frequency.

33. The device according to claim 20, wherein there are provided second detecting means for said chemical and/or physical quantity for the first and/or second ingredient, the second detecting means having respective connecting means to said control means comprising
a respective wireless data transmission circuit connected to said second detecting means, and
a respective receiving circuit interfaced to said control means.

34. The device according to claim 33, wherein said second detecting means are operatively arranged within the first and/or second duct.

35. The device according to claim 20, wherein the mixing area comprises a supply nozzle defining a chamber for the passage of the mixture, the first detecting means acting within said chamber.

36. The device according to claim 35, wherein said receiving circuit is fastened to a component of the body of the device supporting the supply nozzle.

37. A device for measuring or controlling a fluid, in particular the flow rate or amount thereof, comprising at least
an impeller having a central portion or hub from which ex-tends at least a blade, the hub being associated to a rotation pin, the impeller being mounted into a duct having an inlet and an out-let for the fluid;
detecting means for the rotation of the impeller, so as to determine an amount of fluid passing said inlet to said outlet,
wherein
said detecting means comprise sensor means of the rotation of the impeller, arranged inside said duct,
said sensor means are associated to a wireless data transmission circuit, and
a receiving circuit for receiving said data is arranged outside said duct.

38. The device according to claim 37, wherein said transmission circuit comprises a radio-frequency passive electric circuit without independent power supply.

39. The device according to claim 37, wherein said receiving circuit comprises means for supplying and decoding data transmitted by radio-frequency.

40. The device according to claim 37, wherein said transmission circuit and at least a part of said detecting means are housed in a same envelope.

41. The device according to claim 37, wherein said detecting means comprise a measuring circuit.

42. The device according to claim 37, wherein said receiving circuit is operative for transmitting data by radio-frequency to said transmission circuit.

* * * * *